United States Patent [19]

Cohen

[11] Patent Number: 5,428,039

[45] Date of Patent: Jun. 27, 1995

[54] METHOD FOR ELECTIVELY ACHIEVING REVERSIBLE HYPERPOLARIZED CARDIAC ARREST

[75] Inventor: Neri Cohen, Richmond, Va.

[73] Assignee: The Center for Innovative Technology *, Herndon, Va.

[21] Appl. No.: 190,549

[22] Filed: Feb. 20, 1994

[51] Int. Cl.$^6$ ............... A61K 31/505; A61K 31/44; A61K 31/40; A61K 31/50

[52] U.S. Cl. .................... 514/275; 514/336; 514/337; 514/355; 514/353; 514/414; 514/422

[58] Field of Search ............ 514/275, 336, 337, 353, 514/355, 414, 422

[56] References Cited

U.S. PATENT DOCUMENTS

| | | | |
|---|---|---|---|
| 4,908,378 | 3/1990 | Soll et al. | 514/414 |
| 5,139,789 | 8/1992 | Baumgarten | 424/678 |
| 5,256,688 | 10/1993 | Grover et al. | 514/422 |
| 5,268,374 | 12/1993 | Fung et al. | 514/237.2 |
| 5,278,169 | 1/1994 | Atwal et al. | 514/302 |

FOREIGN PATENT DOCUMENTS 0351767 7/1989 European Pat. Off. .

OTHER PUBLICATIONS

Richer, et al., "Cardiovascular and Biological Effects of K+ Channel Openers, A Class of Drugs with Vasorelaxant and Cardioprotective Properties," Life Sciences, 1990, 47 (19), pp. 1693–1705.

Cohen, et al., "Elective cardiac arrest with a hyperpolarizing adenosine triphosphate-sensitive potassium channel opener," The Journal of Thoracic and Cardiovascular Surgery, Aug. 1993, pp. 317–328.

Cohen, et al., "Hyperpolarized Elective Cardiac Arrest with an ATP-Sensitive Potassium Channel Opener," Pace, vol. 16, Apr. 1993, Part II, p. 79.

Tips, "K+ channel openers and 'natural' cardioprotection," Jul. 1992, vol. 13, pp. 269–271.

Auchampach et al., "The New K+ Channel Opener Aprikalim (RP52891) Reduces Experimental...," J. Pharmacol. Exp. Ther., 259(2), 961–967 (1991).

Arena et al., "Activation of ATP-sensitive K+ Channels in heart cells by pinacidil . . . ," Am. J. Physiol., 257(6, Pt. 2), H2092–H2096 (1989).

Minkes et al., "Analysis of pulmonary & systemic vascular responses to cromakalim,". . . Am. J. Physiol. 260 (3, Pt. 2) H957 H966 (1991).

Escande et al., "The potassium channel opener cromakalim (BRL34915) activates . . . ," Biochem. Biophys. Pres. Commun., 154(2) 620–5 (1988).

Sanguinetti et al., "BRL 34915 (cromakalim) activates ATP-sensitive K+ current in cardiac muscle," Proc. Natl. Acad. Sci USA, 85 (21), 8360–8364 (1988).

Ripoll et al., "Modulation of ATP-Sensitive K+ Channel Activity & Contractile Behavior in Mammalian . . . ," J. Pharmacol. Exp. Ther., 255(2), 429–435, (1990).

Satoh et al., "Cardioprotective Actions of ATP-Sensitive K+ Channel Openers (Cromakalim . . . ," J. Nara Med. Ass., 44, 37–46, (1993).

Primary Examiner—Gary E. Hollinden
Assistant Examiner—Mary Cebulak
Attorney, Agent, or Firm—Whitham, Curtis, Whitham & McGinn

[57] ABSTRACT

While performing cardiopulmonary bypass, the aorta is cross-clamped and the beating heart is stopped by introducing of an ATP-dependent potassium channel opening agent. The infusion into the coronary circulation shortens the cardiac action potential thereby arresting the heart muscle at a hyperpolarized membrane potential. This maintains the heart in a state of minimal metabolic requirement, thereby preserving transmembrane ionic gradients, intercellular energy stores and cellular integrity. Cardiac arrest is reversed simply by flushing the heart by the coronary circulation upon removal of the aortic cross-clamp. This use is also germane to organ preservation during transport for transplantation. For example, the donor heart is arrested using an ATP-dependent potassium channel opening agent, it is then removed and transported to the recipient and transplanted. Cardiac arrest is reversed by reperfusing the orthotropic graft.

15 Claims, No Drawings

METHOD FOR ELECTIVELY ACHIEVING REVERSIBLE HYPERPOLARIZED CARDIAC ARREST

BACKGROUND OF THE INVENTION

1. Field of the Invention

This invention generally relates to a method for safely stopping the normal heartbeat in order to perform cardiac, aortic, neurovascular and cardiopulmonary organ transplant surgery and other related operations. More particularly, the invention provides a simplified myocardial protection strategy wherein the heart is stopped using adenosine triphosphate (ATP) dependent channel opening agents to shorten the cardiac action potential and hyperpolarize the heart cells. The heart is maintained in a state of minimal metabolic requirement to preserve transmembrane ionic gradients, intercellular energy stores, and cellular integrity during the course of the operation.

2. Description of the Prior Art

Cardiac surgery requires a still and bloodless operative field, therefore necessitating an interruption in the normal blood flow to the heart. The ensuing oxygen deprivation will damage the heart muscle if preservation measures are not instituted. Presently, cardiac surgery operations are performed using a myocardial protection strategy of membrane potential depolarized arrest with increased concentrations of potassium chloride (KCl). Cardioplegia solutions are specially designed solutions which are used during surgery to arrest the heart beat and to place the heart in a state wherein the muscle is at least partially protected from the damaging effects of ischemia. In present surgical practice, the temperature of the heart is typically lowered from the 37° C. normal body temperature to a temperature between 5° C. and 10° C. while perfusing the heart with a cold cardioplegia solution having elevated levels of potassium. The cold temperatures and the elevated levels of potassium act in combination to stop and protect the heart during surgery and, typically, these same conditions are used when transporting the heart for transplantation purposes.

U.S. Pat. No. 5,139,789 to Baumgarten describes the attributes of several cardioplegia solutions in common use today. The Baumgarten patent points out that having controlled potassium and chloride concentrations in the cardioplegia solution, where the product of the potassium and chloride ions in the cardioplegia solution is approximately equal to that found in blood, is important in the control of heart cell swelling during cardioplegia.

Although the advent of modern techniques of cardioplegia and hypothermia have improved and significantly lengthened the safe operating time for complex myocardial revascularization and repair, there has been a marked increase in the incidence of postoperative cardiac arrhythmias, conduction abnormalities, and myocardial injury. Ventricular hypertrophy and reduced myocardial reserves appear clinically to shorten the "safe" time limits of hypothermic cardioplegia. Depolarization of the cardiac cell by a hyperkalemic cardioplegia solution causes derangements in the normal transmembrane distribution of ions, and, most crucially, causes the elevation of intracellular sodium and calcium ions. Recent work has demonstrated that elevated calcium ions produced by an influx of calcium in exchange for sodium ($Na^+$—$Ca^{2+}$ exchange), or directly through the calcium "window current", is the underlying pathology in triggered arrhythmias, reperfusion injury and the "calcium paradox". While hypothermia is used as a component of cardioplegia because it slows the deleterious metabolic effects of depolarization, cardiac cooling itself causes myocardial injury through alterations in cellular volume regulatory mechanisms and the ensuing myocardial edema. Myocardial edema reduces ventricular function by lessening compliance. Furthermore, hypothermia increases the operative time because of the need to cool and rewarm the patient while on cardiopulmonary bypass.

European Patent Application 0,351,767 to Grover discloses the use of potassium channel activators to inhibit myocardial cell necrosis and to maintain the functioning of the heart during regional myocardial ischemia and/or reperfusion. Grover reports that potassium channel activators, when administered during the regional coronary occlusion period and the reperfusion period, improve performance of the myocardial segment at risk for infarction during and after myocardial ischemia. In practice, experiments using a model of rat portal vein tissue showed that the potassium channel activators cause partial hyperpolarization of the membrane potential and a subsequent decrease in the probability of opening of the voltage dependent calcium channels such that the rate of spontaneous muscle contractions is slowed. The treatment scheme utilizes periodic administration of the potassium channel activators to slow muscle twitching. Having the muscle twitching at slower rate during ischemia and reperfusion was demonstrated to result in decreased contractile dysfunction after ischemia.

SUMMARY OF THE INVENTION

It is an object of this invention to provide a new and safe method for electively inducing cardiac arrest so that complex surgical operations can be performed with a reduced risk of myocardial injury.

It is another object of this invention to use ATP dependent potassium channel openers to shorten cardiac action potential and hyperpolarize heart cell membranes.

According to the invention, experiments with rabbits and pigs have demonstrated that administration of ATP dependent potassium channel openers to the heart can induce predictable and sustained electromechanical standstill and cardiac relaxation. The ATP dependent potassium channel openers hyperpolarize heart cell membranes and maintain the heart in minimal metabolic requirement, thereby preserving transmembrane ionic gradients, intracellular energy stores, and cellular integrity. Hyperpolarized arrest provides better distribution of the cardioplegia solution through its coronary vasodilation action, in direct contrast to the vasoconstriction caused by KCl depolarization. Furthermore, because hyperpolarized cardiac arrest can be performed at normal body temperatures, the time for cardiopulmonary bypass can be significantly reduced since the need for cooling and rewarming the heart and patient is avoided.

DETAILED DESCRIPTION OF THE PREFERRED EMBODIMENTS OF THE INVENTION

It has been discovered that cardiac arrest at hyperpolarized cellular membrane potentials, which is the natural resting state of the heart, will meet all the requirements of modern cardioplegia, namely, electromechanical asystole and cardiac relaxation, while preserving the vital integrity of the heart itself. To determine whether activation of ATP-sensitive potassium ($K_{ATP}$) channels by pharmacological agents could produce hyperpolarized arrest, aprikalim and nicorandil, both of which are known ATP dependent potassium channel opening (PCO) agents, were used to arrest the intact beating heart. In a normothermic (37° C.) isolated rabbit heart preparation, aprikalim was found to rapidly shorten the action potential duration and produce cardiac asystole that was maintained during twenty minutes of "no-flow" global ischemia without a rise in end-diastolic pressure. Cardiac rhythm and function were fully restored by reperfusion alone. The developed pressure was 100.6±7.9% of the prearrest value after thirty minutes of reperfusion. In contrast, twenty minutes of unprotected normothermic global ischemia resulted in a 2.7±0.55 mm Hg rise in end-diastolic pressure, and only a 58.2±3.8% recovery of developed pressure after thirty minutes of reperfusion. By way of comparison, twenty minutes of standard hyperkalemic depolarized normothermic arrest was accompanied by a 1.2±0.66 mm Hg rise in end-diastolic pressure, and only 80.8±2.6% recovery of developed pressure after thirty minutes of reperfusion. In order to directly compare hyperkalemic depolarized arrest to PCO induced hyperpolarized cardiac arrest, and to better define the characteristics of PCO hyperpolarized arrest, a fixed (4 mm Hg rise in end-diastolic-pressure-contracture) ischemic injury model was studied. The time to development of the contracture was prolonged by hyperkalemic arrest (35.8±1.7 min.) and significantly more so by PCO arrest (47.0±3.3 min.) when compared to unprotected hearts (24.0±1.2 min.). Moreover, use of aprikalim resulted in significantly better postischemic recovery of function (developed pressure was 69.0±6.7% of prearrest value after thirty minutes of reperfusion) than after no cardioplegia (45.4±7.5%) or standard hyperkalemic cardioplegia (44.3±5.7%).

Hence, pharmacological activation of $K_{ATP}$ channels can result in predictable and sustainable hyperpolarized cardiac arrest that is reversible by reperfusion. This method of cardioplegia was found to fully preserve cardiac electromechanical function following a twenty minute period of global normothermic ischemia. Furthermore, PCO hyperpolarized arrest significantly prolonged the period to the development of contracture as well as afforded a significantly better postischemic recovery of function when compared to either hearts protected with hyperkalemic depolarized arrest or those not protected by any form of cardioplegia.

Several different PCOs are now known. Richer et al., *Life Sciences*, "Cardiovascular and Biological Effects of K+Channel Openers, A Class of Drugs With Vasorelaxant and Cardioprotective Properties", 47(19) pp. 1693–1705 (1990), discusses the chemical structure and activity of a wide variety of PCOs, and that article is herein incorporated by reference. Exemplary PCOs include: aprikalim, cromakalim, lemakalim, pinacidil, nicorandil, minoxidil, bimakalim, celikalim, RP 49356, EP-A-0376524, SR 44866, LP-805, Ro 31-6930, SO121, and HOE-234. The structures of these PCOs are as set forth below:

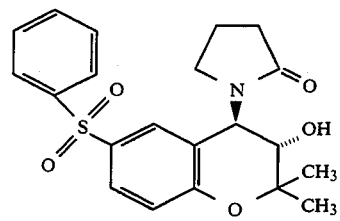
HOR234

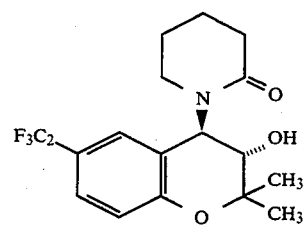
Smith Kline Beecham
HP-A-0376524

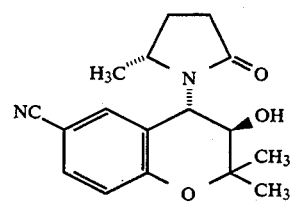
SO121

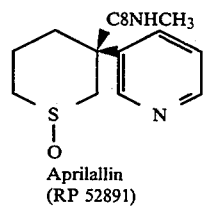
Aprilallin
(RP 52891)

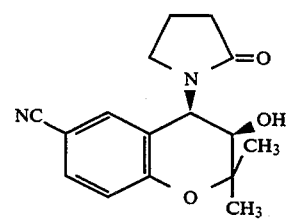
Lemakalin

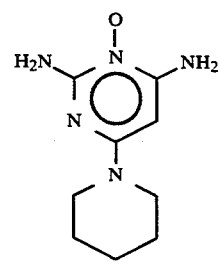
Mihoxidii

-continued

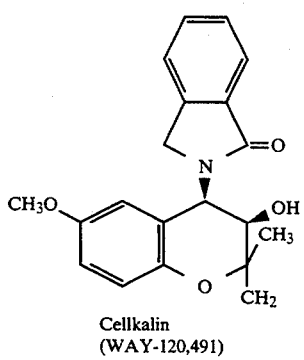

Cellkalin
(WAY-120,491)

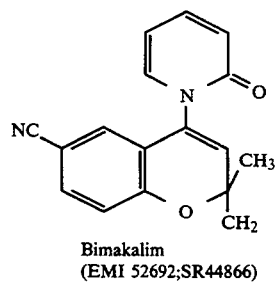

Bimakalim
(EMI 52692;SR44866)

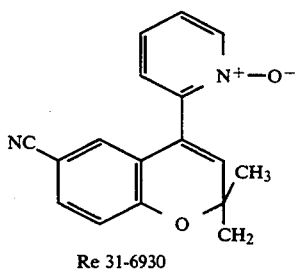

Re 31-6930

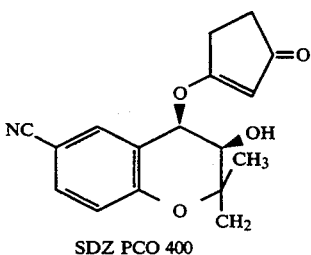

SDZ PCO 400

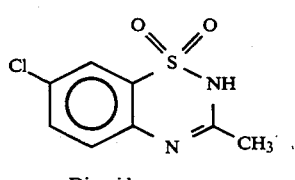

Diaoxide

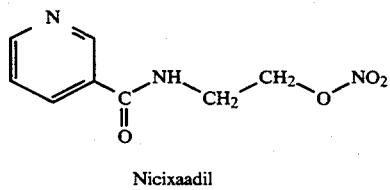

Nicixaadil

-continued

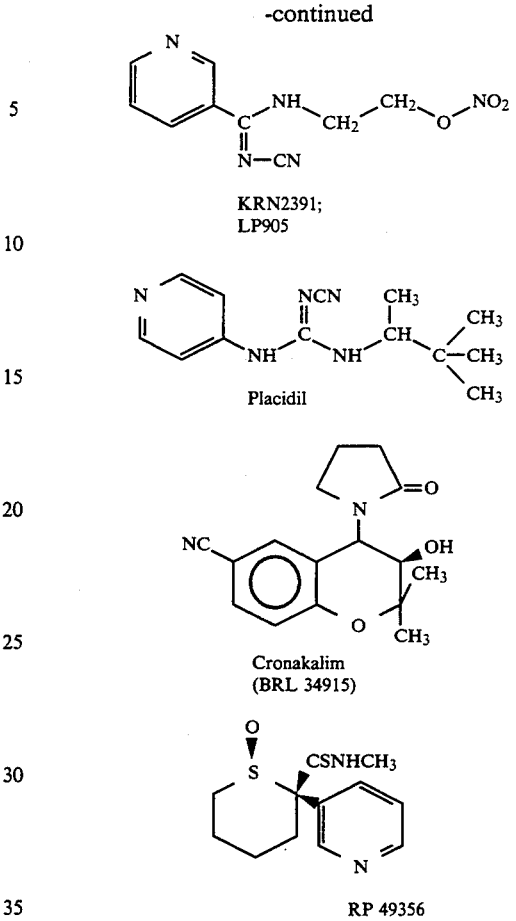

KRN2391;
LP905

Placidil

Cronakalim
(BRL 34915)

RP 49356

While experimental evidence reported below shows that aprikalim and nicorandil can induce reversible, hyperpolarized cardiac arrest in test animals, it is expected that other PCOs can be used within the practice of the invention to achieve similar results.

The hyperpolarized cardiac arrest can be achieved by a cardioplegia solution containing a concentration as low as 10 µM of the PCO; however, using higher concentrations such as 75 µM-150 µM results in longer protection and better recovery of function after cardiac arrest. Toxicity problems are expected when the PCO concentration in the heart is greater than 150 µM. The best results are achieved when the PCO concentration in the heart is approximately 100 µM (e.g., 90 µM-110 µM).

The following examples demonstrate the beneficial effects of an ATP-sensitive PCO during cardiac, aortic, and neurovascular surgery and cardiopulmonary and other organ transplant surgery and other related operations in humans and animals.

EXAMPLE 1

This Example details the experimental results which demonstrate the ability of a PCO to arrest an intact beating heart.

Experimental preparation. Adult New Zealand white rabbits of either sex weighing 3 to 4 kg were anesthetized intramuscularly with acepromazine (2.5 mg/kg), xylazine (2.0 mg/kg), and ketamine (50 mg/kg). Heparin (1000 U/kg) was administered intravenously through an ear vein. A median sternotomy was performed and the heart was rapidly removed. The aorta was cannulated and coronary perfusion instituted on a modified Langendorff apparatus. Retrograde aortic perfusion was performed at 80 cm $H_2O$ with filtered Krebs-Henseleit solution (in millimoles per liter: NaCl, 118.5; $NaHCO_3$, 25; KCl, 3.2; $MgSO_4$, 1.2; $KH_2PO_4$, 1.2; dextrose, 5.5; $CaCl_2$, 2.5) gassed with a mixture of 95% oxygen and 5% carbon dioxide. Perfusate, bath and myocardial temperature were monitored (thermocouple monitor model 0-0544, Shiley, Inc., Irvine, Calif.) continuously with thermocouples (probe model 0112, Shiley), and the column and bath water jacket temperatures were adjusted to maintain myocardial temperature at 37° C. throughout the experiment.

Functional measurements. A latex balloon was placed through the mitral valve into the left ventricle. The balloon was secured with a pursestring suture through the mitral valve annulus. The balloon was connected through fluid-filled polyethylene tubing (inner diameter=0.86 mm) to a pressure transducer (model P23ID, Gould, Inc., Cleveland, Ohio) and amplifier (model 13-4615-50; Gould) and the signal was displayed on an ES1000 recording system (Gould). The zero pressure reference was set at the level of the aortic valve. End diastolic pressure was set to 10 mm Hg by filling the balloon with 1.5 to 3.0 ml of perfusate. Developed pressure was measured as the difference between peak systolic pressure and end-diastolic pressure on the analog records.

Electrophysiologic measurements. The monophasic action potential (MAP) duration recorded with either a suction or a contact electrode provides a good approximation of the action potential duration of a transmembrane recording and gives a representative sample of the transmembrane action potential population of cells underlying the electrode. The MAP faithfully records both the duration and the configuration of the repolarization phase of the transmembrane action potential. Because the asymptotic end of repolarization makes precise measurement of total MAP duration difficult, the MAP duration is usually determined at a repolarization of 90% of total amplitude ($APD_{90}$). Total amplitude (of the measured extracellular voltage) is defined as the distance from the baseline to the crest of the MAP plateau, not its upstroke peak. MAPs were recorded with a 4Fr Langendorff endocardial contact electrode probe (model 141205; EP Technologies, Mountain View, Calif.) placed in the trabeculae of the right ventricular apex through the superior vena cava. Once stabilized, MAPs could be recorded continuously from the same site for periods of up to 3 hours without further manipulation of the catheter or readjustment of the electrode position. The MAP signal was processed through a preamplifier (model 111101; EP Technologies) with an isolated, direct-current (DC)-coupled input with a minimum high-frequency roll-off of 5 kHz, push-button controls for input voltage calibration, and automatic DC-offset compensation. The preamplifier output was connected to the ES1000 recording system (Gould) via a universal bioelectric amplifier (model 13-4615-58; Gould) for simultaneous display of MAP and pressure recordings on a strip-chart recorder. $APD_{90}$ was measured from the analog record displayed at high time resolution (100 mm/sec chart speed) by the methods described earlier. Data was also recorded on VHS videotape (DC to 20 kHz bandwidth) (XR-70, TEAC, Tokyo, Japan) for later off-line analysis.

Experimental protocol. The heart was allowed to recover for 20 to 30 minutes after being instrumented, and stable pressure and MAP recordings were established. Hearts were randomly assigned to either "fixed ischemic time" or "fixed ischemic injury" protocols (described later) and then further randomized to one of three arrest conditions: (1) no cardioplegia, (2) hyperkalemic depolarized arrest, or (3) PCO hyperpolarized arrest. The retrograde perfusion column was clamped, and either 50 ml of normothermic (37° C.) cardioplegic solution was delivered into the aortic root at 80 cm $H_2O$ via a separate column (aprikalim or hyperkalemic [Hi K] groups) or no cardioplegic solution (Krebs-Henseleit solution) was delivered (control group). Depolarizing cardioplegic solution (Hi K) was made by adding concentrated potassium chloride to the Krebs-Henseleit perfusate; final potassium ion concentration was 20 mEq/L. Hyperpolarizing cardioplegic solution was made by adding aprikalim to the Krebs-Henseleit perfusate. The initial aprikalim concentration tested was 100 µM. This concentration was chosen because it represents twice the half maximal effective concentration of the racemic parent compound RP 49356 in biophysical analysis of channel behavior of single cell and patch experiments. In the "fixed ischemic time" experiments, the retrograde aortic perfusion column was unclamped after 20 minutes of normothermic "no-flow" global ischemia, and the heart was reperfused for 30 minutes. In the "fixed ischemic injury" experiments, the retrograde aortic perfusion column was unclamped after development of a contracture (variable time of normothermic "no-flow" global ischemia), and the heart was reperfused for 30 minutes. Pressure, temperature, and MAP were recorded continuously during the entire experiment.

Results. It was found that aprikalim was effective in providing myocardial protection. Table 1 provides a summary of the electrophysical and functional parameters during the "fixed ischemic time" experiments which can be examined to compare the effects of hyperpolarized cardiac arrest, the standard technique of depolarized arrest and untreated hearts (control). The postischemic recovery data was measured at 30 minutes of reperfusion.

TABLE 1

| Group | Prearrest ΔP (mm Hg) | Prearrest $APD_{90}$ (msec) | Arrest ↓ΔP (sec) | Arrest ↓$APD_{90}$ (sec) | Arrest Asystole (sec) | Postischemic recovery EDP (mm Hg) | Postischemic recovery ΔP (mm Hg) | Postischemic recovery % Recovery | Postischemic recovery $ADP_{90}$ (msec) | Fib |
|---|---|---|---|---|---|---|---|---|---|---|
| Control (n = 5) | 110 ± 4 | 120 ± 11 | 142 ± 20 | | | 23 ± 2* | 71 ± 4* | 58 ± 4 | 113 ± 5 | 20% (1/5) |
| Aprikalim (n = 5) | 88 ± 8 | 132 ± 13 | 84 ± 7 | 99 ± 12 | 395 ± 127 | 10 | 89 ± 10 | 101 ± 8 | 134 ± 16 | 60% (3/5) |
| Hyperkalemic | 93 ± 8 | 128 ± 13 | 23 ± 9 | 25 ± 14 | 29 ± 8 | 21 ± 1* | 75 ± 6 | 81 ± 3 | 125 ± 15 | 0% (0/5) |

TABLE 1-continued

| | Prearrest | | Arrest | | | Postischemic recovery | | | | |
|---|---|---|---|---|---|---|---|---|---|---|
| Group | $\Delta P$ (mm Hg) | $APD_{90}$ (msec) | $\downarrow \Delta P$ (sec) | $\downarrow APD_{90}$ (sec) | Asystole (sec) | EDP (mm Hg) | $\Delta P$ (mm Hg) | % Recovery | $ADP_{90}$ (msec) | Fib |
| (n = 5) | | | | | | | | | | |

$\Delta P$ - peak developed pressure;
$APD_{90}$ - action potential duration @ 90% repolarization
$\downarrow \Delta P$ - time to contractile failure to developed pressure <90% of prearrest developed pressure.
$\downarrow ADP_{90}$ - time to action potential shortening to <90% of prearrest action potential duration
asystole - time to electrical quiescence;
EDP - end-diastolic pressure
% Recovery - (postischemic $\Delta P$/prearrest $\Delta P$) · 100;
Fib - ventricular fibrillation necessitating DC cardioversion
*p < 0.01 versus prearrest value;
  p < 0.05 versus prearrest value
  p < 0.01 versus control value;
  p < 0.05 versus hyperkalemia In the hearts protected with PCO hyperpolarized arrest, immediately after the onset of global ischemia, the coronary arteries were perfused with 50 ml of hyperpolarizing cardioplegic solution, which was a Krebs-Henseleit solution containing 100 µmol/L of aprikalim. It was found that the developed pressure began to decrease immediately after the introduction of the aprikalim solution and was at less than 90% of prearrest value in an average of 84±7 seconds. This corresponds to a shortening of the action potential duration to less than 90% of the prearrest value in 99±12 seconds. The hyperpolarized cardiac arrest was obtained in 395±127 seconds. In addition, it was, found that there was no increase in enddiastolic pressure during the ischemic period. It was also found that on reperfusion, there was ventricular fibrillation, which was converted to a normal sinus rhythm with DC cardioversion. In summary, The control group of hearts was subjected to 20 minutes of unprotected global ischemia. The clamping of the retrograde perfusion column resulted in a rapid decline in developed pressure, however, there was continued electrical activity for the entire period of global ischemia. At the end of the global ischemia, there was rise in end-diastolic pressure. Finally, reperfusion was accompanied with a profound rise in end-diastolic pressure and a fall in developed pressure.

The second set of experiments performed were directed to the protective effects of the hyperpolarized arrest during a fixed ischemic injury. The effects of hyperpolarized cardiac arrest was compared to the standard technique of depolarized arrest and to a control group. The data collected on the time to the initiation of a contracture and the subsequent postischemic recovery of function is summarized in Table 2.

TABLE 2

| | Prearrest | | Arrest | | | | Postischemic recovery | | | | |
|---|---|---|---|---|---|---|---|---|---|---|---|
| Group | $\Delta P$ (mm Hg) | $APD_{90}$ (msec) | $\downarrow \Delta P$ (sec) | $\downarrow APD_{90}$ (sec) | Asystole (sec) | Contract (min) | EDP (mm Hg) | $\Delta P$ (mm Hg) | % Recovery | $APD_{90}$ (msec) | Fib |
| Control (n = 6) | 108 ± 6 | 145 ± 13 | 108 ± 10 | | | 24 ± 1 | 31 ± 5 | 50 ± 9 | 45 ± 8 | 135 ± 10 | 17% (1/6) |
| Aprikalim (n = 6) | 117 ± 6 | 112 ± 5 | 80 ± 10 | 95 ± 22 | 409 ± 61 | 47 ± 3 | 19 ± 6 | 80 ± 7 | 69 ± 7 | 136 ± 6 | 100% (6/6) |
| Hyperkalemic (n = 5) | 98 ± 1 | 110 ± 6 | 24 ± 11 | 24 ± 11 | 26 ± 7 | 36 ± 2 | 28 ± 4 | 46 ± 8 | 44 ± 6 | 109 ± 5 | 0% (0/5) | contract - time to 4 mm Hg contracture
*p < 0.01 versus prearrest value;
  p < 0.01 versus control value
  p < 0.01 versus hyperkalemia value
Note: See Table 1 for complete legend the data presented in this table shows that the administration of the aprikalim was successful in shortening the duration of the action potential and in maintaining a cardiac asystole with no rise in the end diastolic pressure. In addition, the cardiac rhythm and function were completely restored by reperfusion alone. Therefore, the aprikalim was successful in protecting ventricular function.

The administration of 50 ml of a depolarizing cardioplegic solution, resulted in a rapid decrease in developed pressure which fell to less than 90% of the prearrest value much more rapidly than either the unprotected (control) or PCO hyperpolarized arrest (aprikalim) groups. The fall in developed pressure and the shortening of the action potential was accompanied by asystole. After the 20 minute period of global ischemia, the end-diastolic pressure had increased. Finally, there was a dramatic rise in end-diastolic pressure and a fall in developed pressure during reperfusion.

As shown in Table 2, the hearts which were protected with PCO hyperpolarized arrest had a prolonged time to the initiation of ischemic contracture when compared to the other groups. In addition, PCO hyperpolarized arrest reduced the reperfusion injury and resulted in a significantly greater recovery of developed pressure after 30 minutes of reperfusion.

In contrast, hyperkalemic depolarized arrest prolonged the amount of time to the initiation of ischemic contracture when compared to the control group. However, the hearts were found to have significant reperfusion injury and the recovery of the developed pressure after 30 minutes was similar to that found in the unprotected (control) hearts.

The unprotected hearts were found to have continued electrical activity for the entire period. In addition, the end diastolic pressure rose during the unprotected global ischemia and reperfusion was accompanied by the profound rise in the end diastolic pressure. There was evidence of reperfusion injury and there was less a 50% recovery of function at the end of the reperfusion.

Dose-response experiments. A direct comparison of the protective effects of increasing doses of aprikalim in the PCO hyperpolarized arrest cardioplegic solution was done in the "fixed ischemic injury" experiments. Twenty-nine hearts were randomly assigned to receive one of six aprikalim concentrations in the cardioplegic solution (see Table 3). Time to development of contracture and postischemic recovery of function were measured as a function of aprikalim concentration. Nonlinear least squares fitting (SigmaPlot 5.0, Jandel Scientific, San Rafael, Calif.) was performed to describe the relationship between each of these parameters of myocardial protection and aprikalim concentration.

Results. The dose response experiments were directed to the measurement of the dose dependence of the cardioprotective characteristics of aprikalim. It was found that an increased dose of aprikalim, the time of protection from ischemic injury was progressively lengthened with a half-maximal aprikalim concentration of 84.5 μmol/L. In addition, an increase in the concentration of aprikalim caused a biphasic response in the postischemic recovery of function. Furthermore, at low doses, an increase in the dose of aprikalim resulted in improved postischemic recovery of function. However, there was a point at which an increased dosage resulted in reduced recovery of function. Table 3 presents a summary of the electromechanical data on the dose dependence of aprikalim protection and the recovery from fixed ischemic injury.

TABLE 3

| Aprikalim dose (μmol/L) | Prearrest | | Arrest | | | Postischemic recovery | | | |
|---|---|---|---|---|---|---|---|---|---|
| | ΔP (mm Hg) | $APD_{90}$ (msec) | ↓ ΔP (sec) | ↓ $APD_{90}$ (sec) | Asystole (sec) | EDP (mm Hg) | ΔP (mm Hg) | $APD_{90}$ (msec) | Fib |
| 10 (n = 5)  | 90 ± 5  | 133 ± 5  | 197 ± 9  | 476 ± 96a | 792 ± 109 | 29 ± 6*  | 51 ± 8*  | 132 ± 4  | 0% (0/5) |
| 50 (n = 6)  | 85 ± 12 | 146 ± 9  | 118 ± 18 | 179 ± 27  | 704 ± 126 | 22 ± 7*  | 53 ± 5*  | 136 ± 12 | 50% (3/6) |
| 100 (n = 6) | 117 ± 3 | 122 ± 5  | 88 ± 18  | 95 ± 22   | 409 ± 61  | 19 ± 6*  | 80 ± 7*  | 136 ± 6  | 100% (6/6) |
| 150 (n = 3) | 103 ± 4 | 127 ± 2  | 74 ± 8   | 70 ± 10   | 387 ± 95  | 18 ± 4*  | 69 ± 4*  | 122 ± 2  | 100% (3/3) |
| 200 (n = 6) | 102 ± 6 | 137 ± 8  | 97 ± 10  | 117 ± 11  | 348 ± 70  | 29 ± 7*  | 63 ± 13* | 130 ± 7  | 83% (5/6) |
| 300 (n = 3) | 91 ± 2  | 110 ± 10 | 49 ± 9   | 46 ± 3    | 219 ± 51  | 33 ± 7*  | 26 ± 9*  | 137 ± 22 | 100% (3/3) |

*$p < 0.01$ versus prearret value
Note: See Table 1 for complete legend

The results of the above described experiments provide evidence that PCO hyperpolarized arrest was able to significantly prolong the time to initiation of ischemic contracture and to provide significantly better postischemic recovery of function than any other form of cardioplegia. The prolongation of the time to initiation of ischemic contracture provides direct evidence that the PCO ameliorates metabolic and ionic abnormalities which are associated with ischemia. Reperfusion after PCO hyperpolarized arrest was accompanied by arrhythmias (fibrillation converted to sinus rhythm with DC cardioversion), a smaller rise in end-diastolic pressure and a progressive increase in peak systolic pressure. It was found that the hyperpolarized state created by the PCO is electrically stable and is maintained until the PCO is washed out by reperfusion. In summary, this data indicates that PCO hyperpolarized arrest affords significantly better myocardial protection than either no protection or hyperkalemic depolarized arrest.

EXAMPLE 2

This Example describes the experimental results and procedures used to demonstrate the beneficial effects of PCO hyperpolarized arrest on a heart during cardiopulmonary bypass in an intact: pig.

Modifications of standard state-of-the-art clinical electrophysiological techniques were employed to measure the effects of surgical ischemia and hyperpolarizing cardioplegic myocardial protection during cardiopulmonary bypass on myocardial tissue. The porcine model was used because of the similarity of the species' coronary circulation and specialized conduction system to that of the human.

Experimental procedure. Pigs weighing 20 to 30 kg were anesthetized with intravenous sodium pentobarbital (30 mg/kg) and maintained on a drip infusion of 2 mg/min throughout the study. Endotracheal intubation was performed through a tracheostomy and the animals mechanically ventilated. The animals underwent median sternotomy and their hearts were suspended in a pericardial cradle. Electrolytes (sodium, potassium, ionized calcium) and arterial blood gases were measured at regular intervals and maintained within the physiologic range. Lead 11 of the surface electrocardiogram (EKG) and systemic blood pressure (PRESSURE) (pressure line in the femoral artery) were monitored continuously and recorded on a Gould ES1000 (Gould Inc., Cleveland, Ohio) monitoring system. A Franz epicardial monophasic action potential (MAP) probe (model 510, EP Technologies, Mountain View, Calif.) was positioned on the epicardial surface of the ventricles overlying the septum. Monophasic action potentials, which accurately reflect intracellular events, particularly the onset of depolarization and the entire repolarization phase of the transmembrane action potential, of stable amplitude and waveform, can be recorded continuously for hours. The monophasic action potential signal was processed through a preamplifier (model 111101, EP Technologies) with an isolated, DC-coupled input with a minimum high-frequency roll-off of 5 kHz, push-button controls for input voltage calibration and automatic DC-offset compensation. The preamplifier output was connected to the ES1000 (Gould Inc.) recording system via a universal bioelectric amplifier (model 13-4615-58, Gould Inc.) for simultaneous display of MAP, EKG and pressure recordings on a strip chart recorder. The animals were placed on cardiopulmonary bypass using a 16Fr right carotid arterial cannula and bicaval cannulation of the superior and inferior vena cavae for venous return. A Pemco 5745 roller pump (Pemco Inc., Independence, Ohio) and capillary membrane oxygenator (Bentley Bos CM50, American Bentley, Irvine, Calif.) were used in the cardiopulmonary bypass circuit which was primed with 2-2.5 liters of blood from a second animal. No antiarrhythmic agents were used in this study and to avoid electrical disturbances there was only limited cardiac manipulation prior to instituting cardiopulmonary bypass. Once on full cardiopulmonary bypass, two four electrode plaques were sutured to the right atrium and left ventricular apex to allow simultaneous recording of unipolar and bipolar epicardial electrograms and for either atrial or ventricular pacing. Both ventricles were vented through the left and right atria respectively. A myocardial temperature probe was placed in the ventricular septum to monitor myocardial temperature continuously. Mean arterial blood pressure was maintained between 60–80 mm Hg and core temperature at 37° C. Pressure, EKG, temperature and MAP were recorded continuously during the entire experiment. The heart was allowed to recover for 20–30 minutes after being instrumented and stable pressure and MAP recordings were established. Prearrest control data were acquired after recovery at 37° C. in the empty beating heart. Left ventricular pacing threshold, effective refractory period, and multiple epicardial electrograms from the pacing plaques were recorded during normal sinus rhythm, atrial and ventricular pacing. Each animal served as its own control undergoing a one hour period of aortic cross-clamping followed by two hours of normothermic reperfusion. The aorta was cross-clamped and cardioplegia delivered into the aortic root antegrade via a separate line. Hyperpolarizing cardioplegia solution was made by adding nicorandil (RP 46417, Rhone-Poulenc Rorer, Antony, FRANCE) to a standard cardioplegia solution perfusate at 37° C. The initial Nicorandil concentration tested was 100 µM chosen as the same concentration of aprikalim (RP 52891) found to be optimal in isolated heart experiments.

In the results of this experiment, in association with the infusion of hyperpolarizing cardioplegia solution, bradycardia, associated with a small transient hypotension and eventually asystole were observed. Cardioplegia was retrieved from the right atrium and the left ventricle and discarded. After one hour of aortic cross-clamping, the cross-clamp was removed and myocardial blood flow restored. At this point, the results of this experiment indicated that cardiac electrical activity returned rapidly and the animal was weaned from cardiopulmonary bypass without the aid of inotropic support at the same systemic pressure as prearrest.

While the invention has been described in terms of its preferred embodiments, those skilled in the art will recognize that the invention can be practiced with modification within the spirit and scope of the appended claims.

I claim:

1. A method for electively achieving reversible cardiac arrest, comprising the steps of:
   interrupting coronary blood circulation surgically in a patient in need of a cardiac or great vessel operation or other operation requiring elective cardiac arrest;
   introducing into the heart of said patient a sufficient amount of an ATP-dependent potassium channel opening agent to cause hyperpolarization of heart cells and arrest the beating of the heart; and
   re-establishing coronary blood circulation in said patient.

2. The method of claim 1 wherein said step of introducing is performed by local administration of said ATP-dependent potassium channel opening agent to the heart.

3. The method of claim 2 wherein said local administration is performed by intracoronary injection.

4. The method of claim 2 wherein said local administration is performed by infusion.

5. The method of claim 1 wherein said ATP-dependent potassium channel opening agent is selected from the group consisting of aprikalim, cromakalim, lemakalim, pinacidil, nicorandil, minoxidil, bimakalim, celikalim, RP 49356, EP-A-0376524, SR 44866, LP-805, Ro 31-6930, SO121, HOE-234, and other agents whose primary action is the opening of cardiac $K_{ATP}$ channels.

6. The method of claim 1 wherein said ATP-dependent potassium channel opening agent is aprikalim.

7. The method of claim 1 wherein said ATP-dependent potassium channel opening agent is nicorandil.

8. The method of claim 1 wherein said ATP-dependent potassium channel opening agent is minoxidil.

9. The method of claim 1 wherein said sufficient amount of an ATP-dependent potassium channel opening agent establishes a concentration in the heart of said ATP-dependent potassium channel opening agent ranging between 75 µM and 150 µM.

10. The method of claim 9 wherein said concentration in the heart of said ATP-dependent potassium channel opening agent ranges between 90 µM and 110 µM.

11. The method of claim 1 wherein said step of introducing into the heart said sufficient amount of an ATP-dependent potassium channel opening agent is performed at approximately normal body temperature.

12. The method of claim 1 wherein said step of introducing into the heart said sufficient amount of an ATP-dependent potassium channel opening agent is performed at hypothermia.

13. The method of claim 1 further comprising the step of performing a cardiac surgical procedure after said step of introducing into the heart said sufficient amount of an ATP-dependent potassium channel opening agent and before said step of reestablishing coronary blood circulation.

14. The method of claim 13 wherein said step of performing said cardiac surgical procedure is performed at approximately normal body temperatures.

15. The method of claim 13 wherein said step of performing said cardiac surgical procedure is performed at hypothermia.

* * * * *